US007074578B2

United States Patent
Kouzarides et al.

(10) Patent No.: US 7,074,578 B2
(45) Date of Patent: Jul. 11, 2006

(54) METHODS AND MEANS OF HISTONE METHYLATION

(75) Inventors: Tony Kouzarides, Cambridge (GB); Helena Santos-Rosa, Cambridge (GB)

(73) Assignee: Chroma Therapeutics LTD, Abingdon (GB)

( * ) Notice: Subject to any disclaimer, the term of this patent is extended or adjusted under 35 U.S.C. 154(b) by 0 days.

(21) Appl. No.: 10/477,225

(22) PCT Filed: May 2, 2002

(86) PCT No.: PCT/GB02/02050

§ 371 (c)(1), (2), (4) Date: Jun. 28, 2004

(87) PCT Pub. No.: WO02/090578

PCT Pub. Date: Nov. 14, 2002

(65) Prior Publication Data

US 2004/0241756 A1 Dec. 2, 2004

(30) Foreign Application Priority Data

May 8, 2001 (GB) ................................. 0111218.4

(51) Int. Cl.
*G01N 33/53* (2006.01)
(52) U.S. Cl. ........................ 435/7.8; 435/7.1; 530/358; 530/388.1
(58) Field of Classification Search ................. 435/7.8, 435/7.1; 530/358; 630/350
See application file for complete search history.

(56) References Cited

U.S. PATENT DOCUMENTS

2004/0053848 A1* 3/2004 Allis et al. ................... 514/14

FOREIGN PATENT DOCUMENTS

EP   1 162 274 A    12/2001
EP   1 162 460 A    12/2001
WO   WO 02/18418    3/2002

OTHER PUBLICATIONS

Strahl et al, PNAS, 1999, vol. 96, No. 26, pp. 14967-14972.*
Allis et al, U.S. Appl. No. 60/227,757, filed Aug. 25, 2000.*
Rea et al; "Regulation of Chromatin Structure by Site-Specific Histone H3 Methyltransferases"; Nature, Macmillan Journal Ltd., London, GB, vol. 406, No. 6796, Aug. 2000, pp. 593-599, XP002154907.
Nislow et al; "Set1, a Yeast Member of the Trithorax Family, Functions in Transcriptional Silencing and Diverse Cellular Process"; Molecular Biology of the Cell, vol. 8, No. 12, Dec. 1997, pp. 2421-2436, XP002248137.
Nagase et al; "Prediction of the Coding Sequences of Unidentified Human Genes VII. The Complete Sequences of 100 New CDNA Clones From Brain Whichcan Code for Large Proteins In Vitro"; DNA Research, Universal Academy Press, JP, vol. 4, No. 2, 1997, pp. 141-150, XP001052821.
Kikuno et al: "Prediction of the Coding Sequences of Unidentified Human Genes. XIV. The Complete Sequences of 100 New Large Proteins In Vitro"; DNA Research, Universal Academy Press, JP, vol. 6, 1999, pp. 197-205, XP000852618.
Santos-Rosa et al; "Active Genes are Tri-Methylated at K4 of Histone H3"; Nature (London), vol. 419,No. 6905, 2002, pp. 407-411, XP002248138.

* cited by examiner

Primary Examiner—Leon B. Lankford, Jr.
Assistant Examiner—Allison M. Ford
(74) Attorney, Agent, or Firm—Nixon & Vanderhye P.C.

(57) ABSTRACT

This invention relates to the methylation of histones, in particular to a previously uncharacterised group of histone H3 methylases which comprise a SET domain and which methylate either lysine 4 within the amino tail of histone H3 or within the histone H3 core. Methylation by these methylases, in particular trimethylation, is shown to be important for transcriptional activity.

1 Claim, 7 Drawing Sheets

(Sequence alignment figure showing Set1 and Set2 family protein sequences including spSet2, scSet2, hSet2, WHSC1, hSet1.1, hSet1.2, and scSet1, with annotated NHSC, GE(x)5Y, and C-rich regions)

Figure 5

1: H3 (1-16) Unmethylated

2: H3 (1-16) K4+K9 Methylated

3: H3 (1-16) K9 Methylated

4: H3 (1-16) K4 Methylated

5: H4 (1-14) Unmethylated

1 ARTKQTARKSTGGKAP 16

$$\text{ART}\overset{\overset{CH_3}{|}}{K}\text{QTAR}\overset{\overset{CH_3}{|}}{K}\text{STGGKAP}$$

$$\text{ARTKQTAR}\overset{\overset{CH_3}{|}}{K}\text{STGGKAP}$$

$$\text{ART}\overset{\overset{CH_3}{|}}{K}\text{QTARKSTGGKAP}$$

1 SGRGKGGKGLGKGG 14

Figure 7

| Gene | ratio | p-value |
|---|---|---|
| PPH3 | -2.14 | 0.002 |
| HAM1 | -1.86 | 0.004 |
| NDD1 | -1.70 | 0.004 |
| SNU23 | -1.70 | 0.005 |
| GDS1 | -1.91 | 0.007 |
| RSR1 | -1.58 | 0.009 |
| PIK1 | -1.74 | 0.009 |
| DLD2 | -1.91 | 0.012 |
| SKT5 | -1.70 | 0.015 |
| NUP170 | -1.62 | 0.016 |
| POP2 | -1.55 | 0.016 |
| CDC50 | -1.55 | 0.017 |
| CDC31 | -1.74 | 0.019 |
| SAP190 | -1.66 | 0.020 |
| TRF4 | -1.78 | 0.022 |
| PAF1 | -1.74 | 0.023 |
| VPS1 | -1.78 | 0.024 |
| NPT1 | -1.62 | 0.025 |

METHODS AND MEANS OF HISTONE METHYLATION

This application is the U.S. national phase of international application PCT/GB02/02050 filed 2 May 2002, which designated the U.S. PCT/GB02/02050 claims priority to GB Application No. 0111218.4 filed 8 May 2001. The entire contents of these applications are incorporated herein by reference.

This invention relates to histone methylation, in particular, to the methylation of specific lysine residues on histone H3 and to the biological effects of such methylation.

DNA in the eukaryotic nucleus is wrapped around a histone-core which is a protein complex involving the four histones H4, H3, H2B and H2A. This DNA-histone structure (nucleosome) is not compatible with gene expression. Re-organisation of the nucleosome is required for transcription factors and RNA polymerase to have access to the DNA for transcription.

Covalent post-translational modifications of the amino-terminal tails of histones regulate the transcriptional 'on' or 'off' states of chromatin and influence chromosome condensation and segregation.

Such modifications include acetylation, phosphorylation and methylation.

Suv39H1 is a methyltransferase which is specific for lysine 9 of histone H3 (Rea et al (2000) Nature 406 593–598). Methylation of lysine 9 by Suv39H1 leads to the recruitment of the HP1 repressor protein (Bannister et al (2001) Nature 410 120–124, Lachner et al (2001) 410 116–120) and the formation of transcriptionally silent heterochromatin.

Suv39H1 has homologues in human (Suv39H2), *Drosophila* (su(var)3–9) and *S. pombe* (clr4). Defects in Suv39H1 and its homologues have been correlated with defects in transcription and aberrant mitotic division and chromosomal mis-segregation.

Expression of the Suv39h1 protein has also been shown to inhibit cell proliferation of mammalian cells and its phosphorylation status is known to change as cells progress from G1 to S.

The Suv39h1 methyltransferase comprises an evolutionarily conserved domain called a SET domain (SUV39 Enhancer of Zest and Trithorax). However, SET domains are also found in other proteins which do not have histone methylase activity (Rea et al. (2000)).

A histone methylase activity has also been identified in yeast Clr4 this activity has been shown to be essential for transcriptional repression (Bannister et al (2001) Nature 410 120–124). Lack of Clr4 methylase activity activates heterochromatically repressed genes at centromeres and may lead to chromosome mis-segregation.

The present inventors have discovered that a group of previously uncharacterised SET domain containing proteins are histone H3 methylases. This group includes *S. cerevisiae* SET1 (YHR119W) and its human homologues hSET1.1P (KIAA0339) and hSET1.2P (KIAA0339) and *S. cerevisiae* SET2 (YJL168C) and its human homologues hSET2 (AJ238403) and WHSC1 (XP_003388).

The present inventors have further discovered that these methylases have activities which are distinct from Suv39h1 and other previously characterised histone methylases. SET1 and related proteins specifically methylate lysine 4 of histone H3 while SET2 and related proteins specifically methylate a lysine residue outside the amino tail region of histone H3 (i.e. a core lysne residue).

Various aspects of the present invention provide for the use of a SET polypeptide and a histone H3 polypeptide in screening methods and assays for agents which modulate methylation of histone H3 by the SET polypeptide, and which may therefore be useful in the modulating cellular proliferation, for example in treating conditions such as cancer.

In a general aspect, the present invention provides an assay method for an agent with ability to modulate, e.g. disrupt, interfere with, or increase interaction and/or binding of histone H3 with a SET polypeptide, the method including:

(a) bringing into contact a SET polypeptide and a histone H3 polypeptide; and, (b) determining binding and/or interaction between the histone H3 polypeptide and the SET polypeptide.

An assay may be carried out in the presence of a test compound under conditions in which, in the absence of the test compound, the SET polypeptide will interact or bind with histone H3.

The precise format of the assay of the invention may be varied by those of skill in the art using routine skill and knowledge. For example, the interaction between the polypeptides may be studied in vitro by labelling one with a detectable label and bringing it into contact with the other which has been immobilised on a solid support.

Suitable detectable labels include $^{35}$S-methionine which may be incorporated into recombinantly produced peptides and polypeptides. Recombinantly produced peptides and polypeptides may also be expressed as a fusion protein containing an epitope which can be labelled with an antibody.

Fusion proteins may be generated that incorporate six histidine residues at either the N-terminus or C-terminus of the recombinant protein. Such a histidine tag may be used for purification of the protein by using commercially available columns which contain a metal ion, either nickel or cobalt (Clontech, Palo Alto, Calif., USA). These tags also serve for detecting the protein using commercially available monoclonal antibodies directed against the six histidine residues (Clontech, Palo Alto, Calif., USA).

A protein may be immobilized on a solid support using an antibody against that protein bound to a solid support or via other technologies which are known per se. A preferred in vitro interaction may utilise a fusion protein including glutathione-S-transferase (GST). This may be immobilised on glutathione agarose beads. In an in vitro assay format of the type described above, a test compound can be assayed by determining its ability to diminish the amount of labelled peptide or polypeptide which binds to the immobilized GST-fusion polypeptide. This may be determined by fractionating the glutathione-agarose beads by SDS-polyacrylamide gel electrophoresis. Alternatively, the beads may be rinsed to remove unbound protein and the amount of protein which has bound can be determined by counting the amount of label present in, for example, a suitable scintillation counter.

An assay according to the present invention may also take the form of an in vivo assay. The in vivo assay may be performed in a cell line such as a yeast strain in which the relevant polypeptides or peptides are expressed from one or more vectors introduced into the cell.

Various methods and uses of modulators which inhibit, potentiate, increase or stimulate methylation of histone H3 by a SET polypeptide are provided as further aspects of the present invention.

The purpose of disruption, interference with or modulation of the methylation of histone H3 by a SET polypeptide may be to modulate cellular functions such as transcription and proliferation which are mediated by virtue of such methylation, such as transcription, as discussed above and further below.

A method of screening for a substance which modulates activity of a SET polypeptide may include contacting one or more test substances or agents with the SET polypeptide in a suitable reaction medium, testing the activity of the treated polypeptide and comparing that activity with the activity of the polypeptide in comparable reaction medium untreated with the test substance, substances or agent. A difference in activity between the treated and untreated SET polypeptides is indicative of a modulating effect of the relevant test substance or substances.

Thus another aspect of the present invention provides an assay method for an agent with ability to modulate, e.g. disrupt, interfere with, increase or stimulate the histone H3 methylase activity of a SET polypeptide, the method including:

(a) bringing into contact a SET polypeptide and a test compound; and,
(b) determining the histone H3 methylase activity of the SET polypeptide.

An assay may be carried out under conditions in which, in the absence of the test compound, the SET polypeptide will possess histone H3 methylase activity. Histone H3 methylase activity may be determined as described herein.

The SET polypeptide and the test compound may, for example, be brought into contact in the presence of a histone H3 polypeptide. Histone H3 methylase activity may then be determined by determining the presence of one or more methyl groups at a lysine residue of the histone H3 polypeptide.

In another aspect, the present invention provides a method for identifying and/or obtaining an agent with ability to modulate, e.g. disrupt, inhibit, interfere with, increase or stimulate methylation of histone H3 by a SET polypeptide, the method including:

(a) bringing into contact a SET polypeptide and a histone H3 polypeptide in the presence of a test compound; and,
(b) determining methylation of the histone H3 polypeptide.

An assay may be carried out under conditions in which, in the absence of the test compound, the SET polypeptide will methylate histone H3.

Determining methylation of the histone H3 polypeptide may comprise determining the presence or absence of one or more methyl groups on a lysine residue of said histone H3 polypeptide, for example lysine 4 or a core lysine residue.

Where the SET polypeptide is a SET1 polypeptide, methylation of the lysine 4 residue of histone H3 may be determined. Where the SET polypeptide is a SET2 polypeptide, methylation of a lysine residue selected from the group consisting of lysine 27, lysine 36, lysine 37, lysine 42, lysine 56, lysine 64, lysine 79, lysine 115, lysine 121, lysine 122 and lysine 125 within the core of histone H3 may be determined. More preferably, where the SET polypeptide is a SET2 polypeptide, methylation of lysine 36 may be determined.

A test compound which increases, potentiates, stimulates, disrupts, reduces, interferes with or wholly or partially abolishes methylation of the histone H3 polypeptide and which may thereby modulate SET polypeptide activity, may thus be identified and/or obtained.

Methylation may be determined according to known methods described herein.

Agents which increase or potentiate methylation of histone H3 may be identified using conditions which, in the absence of a positively-testing agent, prevent methylation. Such agents may be used to potentiate the function of a SET polypeptide and may have an effect, for example, on transcription and/or DNA replication.

In methods of the present invention, a histone H3 polypeptide may brought into contact with a SET polypeptide in the presence of a suitable substrate such as SAM (S-adenosyl-(methyl)-L-methionine). The substrate may be labelled, e.g. (S-adenosyl-(methyl-$^{14}$C)-L-methionine) and the amount of label on the histone H3 after incubation with SET polypeptide determined.

Methods described herein may be useful in determining the presence of, and optionally quantifying, the amount of SET polypeptide in a test sample. This may have a diagnostic or prognostic purpose, e.g. in the diagnosis or prognosis of any medical condition discussed herein (e.g. a proliferative disorder such as cancer) or in the evaluation of a therapy to treat such a condition.

The characterisation of the histone H3 methylase activity of a SET polypeptide as described herein and its role in the regulation of cellular proliferation and transcriptional activity allows the use of materials and methods, such as are disclosed and discussed above, for establishing the presence or absence in a test sample, for example, obtained from an individual, of aberrant, i.e. increased, reduced or abolished SET polypeptide histone H3 methylase activity. Such aberrant activity may be determined as described herein for the purpose of diagnosing a predisposition of an individual to a condition associated with cellular proliferation or for diagnosing an individual as suffering from a condition associated with cellular proliferation, such as cancer. The presence of aberrant SET polypeptide histone H3 methylase activity being indicative of the individual having a condition associated with cellular proliferation or being predisposed i.e. having an increased susceptibility to a condition associated with cellular proliferation.

Aberrant expression may be detected at the protein level, by determining the histone H3 methylase activity of a SET polypeptide, as described herein, for example, the presence or absence or amount of methylase activity or at the nucleic acid level (i.e. DNA or RNA), by determining the presence of a mutant, variant or allele of a SET gene which encodes a SET polypeptide which has aberrant activity or which expresses aberrant i.e. abolished, reduced or increased levels of SET polypeptide. The presence or amount of SET polypeptide expression may be determined by determining the presence and/or amount of mRNA encoding the polypeptide.

In assay methods according to the invention, the amount of test substance or compound which may be added to an assay of the invention will normally be determined by trial and error depending upon the type of compound used. Typically, from about 0.001 nM to 1 mM or more concentrations of putative inhibitor compound may be used, for example from 0.01 nM to 100 µM, e.g. 0.1 to 50 µM, such as about 10 µM. Greater concentrations may be used when a peptide is the test substance. Even a molecule which has a weak effect may be a useful lead compound for further investigation and development.

A test substance, compound or agent used in an assay method as described herein may be comprised in a sample, mixture or extract, for example, a biological sample.

A screening or assay method may include purifying and/or isolating a test substance and/or substance of interest from a mixture or extract, i.e. reducing the content of at least one component of the mixture or extract, e.g. a component with which the test substance is naturally associated. The screening or assay method may include determining the ability of one or more fractions of a test mixture or extract to modulate the methylase activity of the SET polypeptide.

The purification and/or isolation may employ any method known to those skilled in the art.

The precise format of any of the screening or assay methods of the present invention may be varied by those of skill in the art using routine skill and knowledge. The skilled person is well aware of the need to employ appropriate control experiments.

Compounds which may be screened using the assay methods described herein may be natural or synthetic chemical compounds used in drug screening programmes. Extracts of plants, microbes or other organisms, which contain several characterised or uncharacterised components may also be used.

Combinatorial library technology provides an efficient way of testing a potentially vast number of different substances for ability to modulate an interaction. Such libraries and their use are known in the art, for all manner of natural products, small molecules and peptides, among others. The use of peptide libraries may be preferred in certain circumstances.

Methods of determining the methylation of histone H3 by a SET polypeptide and of screening for an agent able to modulate the methylation of histone H3 by a SET polypeptide, include methods in which a suitable end-point is used to assess interaction.

Where the SET polypeptide is a SET1 polypeptide, suitable end points include the determination of the methylation of the lysine 4 residue of histone H3 using methods as described herein.

Where the SET polypeptide is a SET2 polypeptide, suitable end points include the determination of the methylation of histone H3 outside the N terminal 26 amino acids (i.e. at a core lysine residue) using methods as described herein, for example methylation of lysine 36.

Methylation may be determined by any convenient method known to a skilled person. For example, histone H3 polypeptide or variant or derivative thereof, may be immobilised e.g. on a bead or plate, and methylation of the appropriate residue detected using an antibody or other binding molecule which binds the N terminal region of histone H3 with a different affinity when the residue is methylated from when residue is not methylated. Antibodies may also be used to determine the level of methylation e.g. di- or tri-methylation, of a histone H3 lysine residue. Antibodies may be obtained by means of any standard technique as discussed elsewhere herein, e.g. using a methylated peptide (such as an N terminal fragment of histone H3 or a fragment with the N terminal amino acids deleted).

Binding of a molecule which discriminates between the methylated and non-methylated form of a histone H3 polypeptide or between different degrees of methylation may be assessed using any technique available to those skilled in the art, which may involve determination of the presence of a suitable label.

Methylation may also be assayed in solution, e.g. as described in Rea et al (2000), Nature, 406: 593–599. Briefly, 10 µg of free histone substrate (mixture of H1, H2, H3, and H4; Boehringer Mannheim) is mixed with 300 nCi S-adenosyl-[methyl-$^{14}$C]-L-methionine (25 µCi ml$^{-1}$) (Amersham) as methyl donor in methylase activity buffer (50 mM Tris.HCl pH8.5, 20 mM KCl, 10 mM MgCl$_2$, 10 mM β-mercaptoethanol, 250 mM sucrose), to give a final volume of 50 µl. 10 µg of SET polypeptide preparation is added and the reaction incubated at 37° C. for 60 mins. The reaction products are then resolved by SDS-PAGE and viewed following fluorography of the gel. Alternatively, following SDS-PAGE, the resolved proteins can be Western blotted to a nitrocellulose membrane, which is then dried and exposed to film.

Methylation may also be determined as described below in the examples.

Of course, the person skilled in the art will design any appropriate control experiments with which to compare results obtained in test assays.

A histone H3 polypeptide may be a full-length histone H3 protein from a eukaryotic cell, such as a yeast or a mammal, for example a human. The term also includes fragments of the full-length protein sequence, such as fragments which comprise the lysine 4 residue, for example, fragments comprising the N terminal residues of the full length protein. Other fragments may comprise residues from the core of histone H3, i.e. outside the amino tail region, such as fragments which comprise a lysine residue selected from the group consisting of lysine 27, lysine 36, lysine 37, lysine 42, lysine 56, lysine 64, lysine 79, lysine 115, lysine 121, lysine 122 and lysine 125, for example, a fragment comprising lysine 36.

A SET polypeptide may be a full-length SET protein or a fragment thereof which retains the methylase activity of the full length SET protein, for example a polypeptide which comprises the SET domain.

Examples of SET domains are shown in FIGS. 1 and 2. A SET domain may comprise three conserved motifs; NHSC, GEXSY and Erich (Rhea S. et al (2000) Nature 406 593–599). These motifs are indicated in FIG. 1 and FIG. 2.

A SET domain of a SET1 polypeptide may further comprise conserved motifs I, II, III, IV and V as indicated in FIG. 1 and FIG. 2.

A SET polypeptide may be a member of the SET1 or the SET2 families of histone H3 methylases (HMTs).

SET1 polypeptides specifically methylate the lysine 4 residue of histone H3 and include *S. cerevisiae* SET1 (Database Accession Number YHR119W), *S. pombe* SET1 (SPCC306.04c), hSET-1P (Human: KIAA0339), hSET-2P (Human: KIAA1076), HRX, TRX2, KIAA1090, and ALR (all on public databases). SET1 polypeptides may comprise a SET domain having greater than 35%, greater than 40%, greater than 45% or greater than 50% sequence identity with the SET domain of *S. cerevisiae* SET1.

An aspect of present invention provides a SET1 polypeptide which methylates lysine 4 of a histone H3 polypeptide.

SET2 polypeptides specifically methylate a lysine residue selected from the group consisting of lysine 27, lysine 36, lysine 37, lysine 42, lysine 56, lysine 64, lysine 79, lysine 115, lysine 121, lysine 122 and lysine 125 i.e. a core lysine of histone H3 outside the N terminal 26 amino acid tail. More preferably, a SET2 polypeptide specifically methylates lysine 36. SET2 polypeptides include *S. cerevisiae* SET2 (YJL168C), *S. pombe* SET2 (SPAC29B12), hSET2 (AJ238403), WHSC1 (XP_003388), Q9H6H8, NSD1, NSD3 and ASH1 (all on public databases).

Another aspect of present invention provides a SET2 polypeptide which methylates a core lysine residue of a histone H3 polypeptide.

SET2 polypeptides may comprise a SET domain having greater than 35%, greater than 40%, greater than 45% or greater than 50% sequence identity with the SET domain of *S. cerevisiae* SET2.

A histone H3 or SET polypeptide may include any suitable fragment, variant, derivative, allele or homologue of histone H3 or the SET polypeptide, which may be employed in a method described herein. Suitable fragments, variants or derivatives of histone H3 retain the biological activity of being methylated by a SET polypeptide i.e. they include the appropriate sites of methylation by the SET polypeptide, for example, lysine 4 or other target residues within the histone H3 core (outside the amino tail residues 1 to 26), for example lysine 36. Suitable variants or derivatives of a SET polypeptide retain the histone H3 methylase activity.

A polypeptide which is an amino acid sequence variant, allele, derivative or mutant of an amino acid sequence described herein may comprise an amino acid sequence which shares greater than about 60% sequence identity with the sequence shown, greater than about 70%, greater than about 80%, greater than about 90% or greater than about 95%. The sequence may share greater than about 70% similarity, greater than about 80% similarity, greater than about 90% similarity or greater than about 95% similarity with the amino acid sequence described herein.

For amino acid "homology", this may be understood to be similarity (according to the established principles of amino acid similarity, e.g. as determined using the algorithm GAP (as described below) or identity.

Amino acid similarity is generally defined with reference to the algorithm GAP (Accelerys, formerly Genetics Computer Group, Madison, Wis.). GAP uses the Needleman and Wunsch algorithm to align two complete sequences that maximizes the number of matches and minimizes the number of gaps. Generally, the default parameters are used, with a gap creation penalty=12 and gap extension penalty=4. Use of GAP may be preferred but other algorithms may be used, e.g. BLAST (which uses the method of Altschul et al. (1990) *J. Mol. Biol.* 215: 405–410), FASTA (which uses the method of Pearson and Lipman (1988) *PNAS USA* 85: 2444–2448), or the Smith-Waterman algorithm (Smith and Waterman (1981) *J. Mol Biol.* 147: 195–197), generally employing default parameters.

Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Particular amino acid sequence variants may differ from a sequence described herein by insertion, addition, substitution or deletion of 1 amino acid, 2, 3, 4, 5–10, 10–20 20–30, 30–50, 50–100, 100–150, or more than 150 amino acids.

Sequence comparison may be made over the full-length of the relevant sequence shown herein, or may more preferably be over a contiguous sequence of about or greater than about 20, 25, 30, 33, 40, 50, 67, 133, 167, 200, 233, 267, 300, 333, 400 or more amino acids, compared with the relevant amino acid sequence.

As described above, peptides which include or consist of fragments of a full-length SET protein are encompassed within the term 'SET polypeptide' as defined herein. Where the SET polypeptide is a fragment of the full-length protein, suitable fragments are generally those which retain the methylase activity of the full-length polypeptide and are capable of methylating histone H3, except where otherwise stated.

A further aspect of the present invention provides a fragment of a full-length SET polypeptide as described herein, said fragment having histone H3 methylase activity.

Preferably such a fragment comprises the SET methylase domain.

A suitable fragment preferably methylates histone H3 outside lysine 9, more preferably at lysine 4 or a lysine residue selected from the group consisting of lysine 27, lysine 36, lysine 37, lysine 42, lysine 56, lysine 64, lysine 79, lysine 115, lysine 121, lysine 122 and lysine 125 i.e. a core lysine residue of histone H3 located outside the first 26 N terminal amino acids, for example, the central and C terminal regions, such as lysine 36.

A fragment of a SET polypeptide includes a fragment of a SET1 polypeptide, which may be any member of the SET1 family, including hSET-1P (human KIAA0339) and hSET-2P (human KIAA1076) and a fragment of a SET2 polypeptide, which may be any member of the SET2 protein family, including hSET2-1, hSET2-2, hSET2-3 and WHSC1.

Another aspect of the present invention provides an isolated nucleic acid molecule comprising a nucleotide sequence which encodes a SET polypeptide. A SET polypeptide may include a fragment of a full-length SET polypeptide sequence described herein.

Such a nucleotide sequence may be operably linked to a heterogeneous regulatory element, such as a promoter or enhancer element. A nucleotide sequence encoding a SET polypeptide as described above may be comprised within a vector, in particular an expression vector.

Vectors comprising nucleic acid encoding a SET polypeptide may be transformed into a suitable host cell as described above to provide for expression of the SET polypeptide. Thus, in a further aspect the invention provides a process for preparing a SET polypeptide which includes cultivating a host cell transformed or transfected with an expression vector as described above under conditions to provide for expression by the vector of a coding sequence encoding the SET polypeptide, and recovering the expressed polypeptide. Polypeptides may also be expressed in in vitro systems, such as reticulocyte lysate.

Following production of a SET polypeptide, it may be tested for histone H3 methytransferase activity, e.g. by determination of methylation of lysine 4 or a core lysine residue of histone H3 selected from the group consisting of lysine 27, lysine 36, lysine 37, lysine 42, lysine 56, lysine 64, lysine 79, lysine 115, lysine 121, lysine 122 and lysine 125, preferably lysine 36 as described herein on incubation of the polypeptide with a histone H3 polypeptide.

Thus the present invention also provides a method of producing a SET polypeptide comprising;
expressing a SET polypeptide from encoding nucleic acid, and;
determining the methyltransferase activity of the expressed SET polypeptide.

The methyltransferase activity may include the methylation of a histone H3 residue other than lysine 9, for example lysine 4 or a lysine residue selected from the group consisting of lysine 27, lysine 36, lysine 37, lysine 42, lysine 56, lysine 64, lysine 79, lysine 115, lysine 121, lysine 122 and lysine 125 i.e. a core lysine residue of histone H3 located outside the first 26 N terminal amino acids, for example lysine 36. Methyltransferase activity may also include the di- or tri-methylation of such a residue.

It is not necessary to use the entire proteins for assays of the invention which test for binding between two molecules. Fragments may be generated and used in any suitable way known to those of skill in the art. Suitable ways of generating fragments include, but are not limited to, recombinant expression of a fragment from encoding DNA. Such fragments may be generated by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Small fragments (e.g. up to about 20 or 30 amino acids) may also be generated using peptide synthesis methods which are well known in the art.

The skilled person can use the techniques described herein and others well known in the art to produce large amounts of peptides, for instance by expression from encoding nucleic acid.

Methods of obtaining agents able to modulate the histone H3 methylation activity of SET polypeptides include methods wherein a suitable end-point is used to assess interaction in the presence and absence of a test substance.

For methylation assays, a histone H3 or SET polypeptide which is a full-length protein, truncated portion, or a portion of fused to another protein (e.g. GST), or a suitable variant or derivative of any of these, may be used.

Peptide methylation assays may use peptides that comprise the region of histone H3 which is methylated. For a SET1 polypeptide, this may include the N-terminal region of histone H3 comprising lysine 4.

For a SET2 polypeptide, this may include a lysine residue selected from the group consisting of lysine 27, lysine 36, lysine 37, lysine 42, lysine 56, lysine 64, lysine 79, lysine 115, lysine 121, lysine 122 and lysine 125, i.e. a core lysine residue of histone H3 located outside the first 26 N terminal amino acids, for example, the central and C terminal regions. Preferably, for a SET2 polypeptide, this may include lysine 36.

The methylation of histone H3 may be assayed by any of a variety of procedures such as discussed below and may be adapted to high throughput screening approaches. Of particular interest is the methylation of the lysine 4 residue of histone H3 by hSET-1P (human KIAA0339) and/or hSET-2P (human KIAA1076) and methylation in the central and/or C terminal portions (i.e. the core) of histone H3 by hSET2 (AJ238403)and/or WHSC1 (XP_003388).

A method of the present invention may comprise identifying and/or obtaining a test compound which modulates the histone H3 methylase activity of a SET polypeptide.

Following identification of a test compound which is an agent or modulator as described herein, it may be investigated further. For example, a compound, substance or molecule which tests positive for ability to modulate methylation of the appropriate residue of histone H3 and/or the methylase activity of a SET polypeptide may be isolated, purified and/or manufactured. A method of the present invention may thus comprise isolating and/or purifying and/or manufacturing or synthesising the test compound.

Furthermore, the test compound may be used in preparation, i.e. manufacture or formulation, of a composition such as a medicament, pharmaceutical composition or drug. This may be administered to individuals. A method of the present invention may thus comprise formulating said compound with a pharmaceutically acceptable excipient as described herein.

In various aspects, the present invention thus provides a modulator identified and/or obtained by a screening method of the invention, e.g. a substance which inhibits or reduces, increases or potentiates the histone H3 methylase activity of a SET polypeptide.

Following identification of a modulator, the substance may be purified and/or investigated further and/or manufactured. A modulator may be used to obtain peptidyl or non-peptidyl mimetics, e.g. by methods well known to those skilled in the art and discussed herein. It may be used in a therapeutic context as discussed below.

Agents according to the present invention useful in modulating the methylation of histone H3 and therefore one or more of its functions within the chromatin, may modulate the methylase activity of the SET polypeptide. Such agents may specifically inhibit the ability of the SET polypeptide to methylate the appropriate residue of histone H3 or provide the appropriate level of methylation. Assays and screens for such agents are provided in accordance with the present invention, along with the agents themselves and their use in modulating the methylation and thereby the function of histone H3.

An agent able to inhibit methylation of histone H3 by a SET polypeptide may include a substance able to affect the catalytic properties of the enzymatically active site of the methylase. An inhibitor of methylation may interact with the SET polypeptide within the SET methylase domain. Residues within this domain are involved in interaction with histone H3 and catalysis of the methylation. Residues outside of the domain may also be involved in interacting with histone H3 and agents which interfere with such interaction may also affect the methylation as discussed elsewhere herein.

Agents useful in accordance with the present invention may be identified by screening techniques which involve determining whether an agent under test inhibits or disrupts the methylation by a SET polypeptide of the histone H3 polypeptide.

One class of putative modulator compounds can be derived from the SET polypeptide sequence and/or a ligand with which it interacts, such as histone H3. Peptide fragments of these polypeptides or alleles, mutants or derivatives of such fragments are described herein. Nucleic acid encoding such peptides, vectors and host cells containing such nucleic acid, and methods of expressing nucleic acid encoding such peptides are further aspects of the present invention.

Where the histone H3 polypeptide is a fragment of the full length protein, suitable fragments are those which contain the appropriate residue which is methylated by a SET polypeptide in the full-length polypeptide, and are themselves capable of being methylated by a SET polypeptide. Smaller fragments, and analogues and variants of these fragment may similarly be employed, e.g. as identified using techniques such as deletion analysis or alanine scanning.

Fragments methylated by a SET1 polypeptide include fragments comprising the N terminal of histone H3, in particular lysine 4. Fragments methylated by a SET2 polypeptide include fragments comprising a lysine residue selected from the group consisting of lysine 27, lysine 36, lysine 37, lysine 42, lysine 56, lysine 64, lysine 79, lysine 115, lysine 121, lysine 122 and lysine 125 i.e. a core lysine residue of histone H3 located outside the first 26 N terminal amino acids, in particular lysine 36.

Thus, the present invention provides a SET polypeptide, which is preferably a peptide fragment, which is able to inhibit methylation of histone H3.

Such peptide fragments may be obtained by means of deletion analysis and/or alanine scanning of the relevant protein—making an appropriate mutation in sequence, bringing together a SET polypeptide and a histone H3 polypeptide in the presence of the mutated fragment, and determining methylation of the histone H3 polypeptide. In preferred embodiments, the peptide is short, as discussed below, and may be a minimal portion which is able to interact with the relevant counterpart protein and inhibit methylation.

A "fragment" of a polypeptide generally means a stretch of amino acid residues of at least about five contiguous amino acids, often at least about seven contiguous amino acids, typically at least about nine contiguous amino acids, more preferably at least about 13 contiguous amino acids, and, more preferably, at least about 20 to 30 or more contiguous amino acids. Fragments of a SET polypeptide may include antigenic determinants or epitopes useful for raising antibodies to a portion of the amino acid sequence. Alanine scans are commonly used to find and refine peptide motifs within polypeptides, this involving the systematic replacement of each residue in turn with the amino acid alanine, followed by an assessment of biological activity.

Where the SET polypeptide is a SET1 polypeptide and the histone H3 polypeptide is a fragment, the fragment generally comprises the lysine 4 residue.

Where the SET polypeptide is a SET2 polypeptide and the histone H3 polypeptide is a fragment, the fragment generally comprises a lysine residue selected from the group consisting of selected from the group consisting of lysine 27, lysine 36, lysine 37, lysine 42, lysine 56, lysine 64, lysine 79, lysine 115, lysine 121, lysine 122 and lysine 125 i.e. a core lysine residue of histone H3 located outside the first 26 N terminal amino acids. More preferably the fragment comprises lysine 36.

Peptides in accordance with the present invention tend to be short, and may be about 40 amino acids in length or less, preferably about 35 amino acids in length or less, more preferably about 30 amino acids in length, or less, more preferably about 25 amino acids or less, more preferably about 20 amino acids or less, more preferably about 15 amino acids or less, more preferably about 10 amino acids or less, or 9, 8, 7, 6, 5 or less in length. Peptides according to the present invention may be about 10–40 amino acids in length, about 5–10, about 10–15, about 10–20, about 10–30, about 20–30, or about 30–40 amino acids in length. Peptides which are histone H3 fragments generally include one or more of the relevant lysine residues.

The present invention also encompasses peptides which are sequence variants or derivatives of a wild-type SET polypeptide sequence. Peptides which are variants of wild-type SET polypeptide sequence retain the ability to modulate methylation of histone H3 by a SET polypeptide.

A SET polypeptide or histone H3 polypeptide may be a peptide or polypeptide which may include an amino acid sequence which differs by one or more amino acid residues from the wild-type amino acid sequence, by one or more of addition, insertion, deletion and substitution of one or more amino acids. Thus, variants, derivatives, alleles, mutants and homologues, e.g. from other organisms, are included.

Preferably, the amino acid sequence shares homology with a region of the relevant SET polypeptide or histone H3 polypeptide as referenced herein, preferably at least about 60%, or 70%, or 75%, or 80%, or 85%, 90% or 95% homology. Thus, a peptide fragment of a SET polypeptide or histone H3 polypeptide may include 1, 2, 3, 4, 5, greater than 5, or greater than 10 amino acid alterations such as substitutions with respect to the wild-type sequence.

A derivative of a peptide for which the specific sequence is disclosed herein may be in certain embodiments the same length or shorter than the specific peptide. In other embodiments the peptide sequence or a variant thereof may be included in a larger peptide, as discussed above, which may or may not include an additional portion of SET polypeptide or histone H3 polypeptide. 1, 2, 3, 4 or 5 or more additional amino acids, adjacent to the relevant specific peptide fragment of SET polypeptide or histone H3 polypeptide, or heterologous thereto may be included at one end or both ends of the peptide.

Antibodies directed to the site of binding of SET polypeptides form another class of putative modulators of SET methylase activity. Candidate inhibitor antibodies may be characterised and their binding regions determined to provide single chain antibodies and fragments thereof which are responsible for disrupting the binding.

Antibodies may be obtained using techniques which are standard in the art. Methods of producing antibodies include immunising a mammal (e.g. mouse, rat, rabbit, horse, goat, sheep or monkey) with a SET polypeptide. Antibodies may be obtained from immunised animals using any of a variety of techniques known in the art, and screened, preferably using binding of antibody to antigen of interest. For instance, Western blotting techniques or immunoprecipitation may be used (Armitage et al., 1992, Nature 357: 80–82). Isolation of antibodies and/or antibody-producing cells from an animal may be accompanied by a step of sacrificing the animal.

As an alternative or supplement to immunising a mammal with a peptide, an antibody specific for a SET polypeptide may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with any of the proteins (or fragments), or may be one constructed using sequences obtained from an organism which has been exposed to the antigen of interest.

Antibodies according to the present invention may be modified in a number of ways. Indeed the term "antibody" should be construed as covering any binding substance having an immunoglobulin binding domain with the required specificity. Thus the invention covers antibody fragments, derivatives, functional equivalents and homologues of antibodies, including synthetic molecules and molecules whose shape mimics that of an antibody enabling it to bind an antigen or epitope.

A hybridoma producing a monoclonal antibody according to the present invention may be subject to genetic mutation or other changes. It will further be understood by those skilled in the art that a monoclonal antibody can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP184187A, GB 2188638A or EP-A-0239400. Cloning and expression of chimeric antibodies are described in EP-A-0120694 and EP-A-0125023.

Hybridomas capable of producing antibody with desired binding characteristics are within the scope of the present invention, as are host cells, eukaryotic or prokaryotic, containing nucleic acid encoding antibodies (including antibody fragments) and capable of their expression. The invention also provides methods of production of the antibodies including growing a cell capable of producing the antibody under conditions in which the antibody is produced, and preferably secreted.

The reactivities of antibodies on a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule. The mode of determining binding is not a feature of the present invention and those skilled in the art are able to choose a suitable mode according to their preference and general knowledge.

Antibodies may also be used in purifying and/or isolating SET polypeptide, for instance following production of the polypeptide by expression from encoding nucleic acid. Antibodies may be useful in a therapeutic context (which may include prophylaxis) to disrupt binding of a SET polypeptide to histone H3 and inhibit the methylation of the target lysine residue. Antibodies can for instance be microinjected into cells, e.g. at a tumour site, subject to radio- and/or chemotherapy (as discussed already above). Antibodies may be employed in accordance with the present invention for other therapeutic and non-therapeutic purposes which are discussed elsewhere herein.

As noted, the agent may be peptidyl, e.g. a peptide which includes a sequence as recited above, or may be a functional analogue of such a peptide.

As used herein, the expression "functional analogue" relates to peptide variants or organic compounds having the same functional activity as the peptide in question, which may interfere with the methylation of the lysine 4 residue of histone H3 by a SET polypeptide. Examples of such analogues include chemical compounds which are modelled to resemble the three dimensional structure of the SET methylase domain in the contact area, and in particular the arrangement of the key amino acid residues.

In a further aspect, the present invention provides the use of a SET polypeptide, in particular a peptide fragment, which is capable of methylating the lysine 4 residue of histone H3, in a method of designing a peptide or non-peptidyl mimetic, which mimetic is able to interact with the SET polypeptide active site and modulate the methylation of the lysine 4 residue by the SET polypeptide.

Accordingly, the present invention provides a method of designing a mimetic, for example of a histone H3 amino terminal fragment, which has the biological activity of modulating the methylation of the lysine 4 residue by the SET polypeptide, said method comprising:
  (i) analysing a substance to determine the amino acid residues essential and important for the biological activity to define a pharmacophore; and,
  (ii) modelling the pharmacophore to design and/or screen candidate mimetics which modulate the methylation as described.

Suitable modelling techniques are known in the art. This includes the study of the bonding between SET and histone H3 and the design of compounds which contain corresponding functional groups arranged in such a manner that they could reproduce that bonding.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, for instance SET polypeptides may not be well suited as active agents for oral compositions as they tend to be quickly degraded by proteases in the alimentary canal.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled according to its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of the above approach, the three-dimensional structure of a ligand and its binding partner are modelled. This can be especially useful where the ligand and/or binding partner change conformation on binding, allowing the model to take account of this the design of the mimetic.

A compound found to have the ability to affect SET methylase activity has therapeutic and other potential in a number of contexts, as discussed. For therapeutic treatment such a compound may be used in combination with any other active substance, e.g. for anti-tumour therapy another anti-tumour compound or therapy, such as radiotherapy or chemotherapy.

An agent identified using one or more primary screens (e.g. in a cell-free system) as having ability to modulate the methylase activity of a SET polypeptide may be assessed further using one or more secondary screens. A secondary screen may involve testing for a biological function of histone H3 methylated at the lysine 4 position or a lysine residue selected from the group consisting of lysine 27, lysine 36, lysine 37, lysine 42, lysine 56, lysine 64, lysine 79, lysine 115, lysine 121, lysine 122 and lysine 125 i.e. a core lysine residue of histone H3 located outside the first 26 N terminal amino acids, preferably lysine 36. Suitable biological functions include the transcriptional activation of a chromatin region or domain which comprises or is associated with the histone H3 polypeptide and/or binding to a regulatory factor such as the NuRD repressor.

Generally, a modulator according to the present invention is provided in an isolated and/or purified form, i.e. substantially pure. This may include being in a composition where it represents at least about 90% active ingredient, more preferably at least about 95%, more preferably at least about 98%. Such a composition may, however, include inert carrier materials or other pharmaceutically and physiologically acceptable excipients. As noted below, a composition according to the present invention may include in addition to an modulator compound as disclosed, one or more other molecules of therapeutic use, such as an anti-tumour agent.

The invention further provides a method of treatment which includes administering to a patient an agent as described herein which interferes with or inhibits the methylation of the target residue of histone H3 (for example lys 4 or a core lys residue) by a SET polypeptide. Exemplary purposes of such treatment are discussed elsewhere herein.

The invention further provides various therapeutic methods and uses of one or more compounds or substances selected from (i) SET polypeptide which is able to bind to histone H3; (ii) a modulator identified by a screening method of the present invention; (iii) a mimetic of any of the above substances which can bind to histone H3 or a SET polypeptide.

The therapeutic/prophylactic purpose of such a method or use may be the modulation, e.g. disruption or interference, of the methylation of histone H3 at residues other than lysine 9. Target residues include lysine 4 for SET1. For a SET2 polypeptide, this may include a lysine residue selected from the group consisting of lysine 27, lysine 36, lysine 37, lysine 42, lysine 56, lysine 64, lysine 79, lysine 115, lysine 121, lysine 122 and lysine 125 i.e. a core lysine residue of histone H3 located outside the first 26 N terminal amino acids, for example, within the central and C terminal regions, preferably lysine 36.

The therapeutic/prophylactic purpose may be:
(i) Cancer treatment, which may for example be in combination with chemotherapy and/or radiotherapy.
(ii) Cancer prophylaxis,
(iii) Treatment of other proliferative disorders described herein e.g. psoriasis, cataracts, multiple myeloma.

In various further aspects, the present invention thus provides a pharmaceutical composition, medicament, drug or other composition for such a purpose, the composition comprising one or more such compounds or substances which modulate the activity of a SET polypeptide as described herein and/or the methylation of histone H3 at a lysine residue other than Lys9, the use of such a substance in a method of medical treatment, a method comprising administration of such a substance to a patient, e.g. for treatment (which may include preventative treatment) of a medical condition, e.g. a condition associated with a defect or disorder in transcriptional control, DNA replication, or cell cycle control, e.g. for treatment of a disorder of cellular proliferation such as restenosis, psoriasis, cataracts, multiple myeloma and cancer, preferably all types of solid cancers and malignant lymphomas and especially leukaemia, skin cancer, bladder cancer, breast cancer, uterus cancer, ovary cancer, prostate cancer, lung cancer, colon cancer, pancreas cancer, renal cancer, stomach cancer and cerebral cancer, use of such a substance in the manufacture of a composition, medicament or drug for administration for such a purpose, e.g. for treatment of a proliferative disorder, and a method of making a pharmaceutical composition comprising admixing such a substance with a pharmaceutically acceptable excipient, vehicle or carrier, and optionally other ingredients.

The substances may be used as sole active agents or in combination with one another or with any other active substance, e.g. for anti-tumour therapy another anti-tumour compound or therapy, such as radiotherapy or chemotherapy.

Whatever the substance used in a method of medical treatment of the present invention, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

A substance or composition may be administered alone or in combination with other treatments, either simultaneously or sequentially dependent upon the condition to be treated, e.g. cancer.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the rouse of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Liposomes, particularly cationic liposomes, may be used in carrier formulations.

Examples of techniques and protocols mentioned above can be found in Remington's Pharmaceutical Sciences, 16th edition, Osol, A. (ed), 1980.

The substance or composition may be administered in a localised manner to a tumour site or other desired site or may be delivered in a manner in which it targets tumour or other cells.

Targeting therapies may be used to deliver the active substance more specifically to certain types of cell, by the use of targeting systems such as antibody or cell specific ligands. Targeting may be desirable for a variety of reasons, for example if the agent is unacceptably toxic, or if it would otherwise require too high a dosage, or if it would not otherwise be able to enter the target cells.

Instead of administering such substances directly, they may be produced in the target cells by expression from an encoding nucleic acid introduced into the cells, e.g. from a viral vector. The vector may be targeted to the specific cells to be treated, or it may contain regulatory elements which are switched on more or less selectively by the target cells.

Nucleic acid encoding the substance e.g. a peptide able to modulate, e.g. interfere with, the methylation of the lysine 4 or core lysine residue of histone H3 by a SET polypeptide, may thus be used in methods of gene therapy, for instance in treatment of individuals, e.g. with the aim of preventing or curing (wholly or partially) a disorder.

Vectors such as viral vectors have been used in the prior art to introduce nucleic acid into a wide variety of different target cells. Typically the vectors are exposed to the target cells so that transfection can take place in a sufficient proportion of the cells to provide a useful therapeutic or prophylactic effect from the expression of the desired peptide. The transfected nucleic acid may be permanently incorporated into the genome of each of the targeted cells, providing long lasting effect, or alternatively the treatment may have to be repeated periodically.

A variety of vectors, both viral vectors and plasmid vectors, are known in the art, see U.S. Pat. No. 5,252,479 and WO 93/07282. In particular, a number of viruses have been used as gene transfer vectors, including papovaviruses, such as SV40, vaccinia virus, herpesviruses, including HSV and EBV, and retroviruses. Many gene therapy protocols in the prior art have used disabled murine retroviruses.

As an alternative to the use of viral vectors in gene therapy other known methods of introducing nucleic acid into cells includes mechanical techniques such as microinjection, transfer mediated by liposomes and receptor-mediated DNA transfer.

Receptor-mediated gene transfer, in which the nucleic acid is linked to a protein ligand via polylysine, with the ligand being specific for a receptor present on the surface of the target cells, is an example of a technique for specifically targeting nucleic acid to particular cells.

A peptide or other substance having an ability to modulate or interfere with the methylation of the lysine 4 or core lysine residue of histone H3 by a SET polypeptide, a nucleic acid molecule which encodes a peptide having that ability, may be provided in a kit, e.g. sealed in a suitable container which protects its contents from the external environment. Such a kit may include instructions for use.

In still further aspects the present invention provides for the purification of a SET polypeptide, or for the purification of a histone H3 polypeptide. The invention also provides for a purified SET polypeptide protein. The purified polypeptide may be about 10% pure, more preferably about 20% pure, more preferably about 30% pure, more preferably about 40% pure, more preferably about 50% pure, more preferably about 60% pure, more preferably about 70% pure, more preferably about 80% pure, more preferably about 90% pure, more preferably about 95% pure, or substantially pure.

In another aspect the present invention provides a method of purifying a SET polypeptide, the method including contacting the SET polypeptide with histone H3 polypeptide.

A mixture of material including SET polypeptide may be contacted against immobilised histone H3 polypeptide (e.g. immobilised either covalently or non-covalently such as via a specific binding molecule such as streptavidin or biotin) and molecules which do not bind to the histone H3 polypeptide are washed off.

Following purification, the SET polypeptide may be used as desired, e.g. in an assay for an agent which modulates its activity, e.g. binding, in raising or obtaining a specific antibody or other binding molecule, or in a therapeutic context.

Other aspects of the present invention relate to the disruption of the interaction between histone H3 and the NuRD complex by the methylation of histone H3 lysine 4 by a SET1 polypeptide.

A method for identifying and/or obtaining an agent which modulates the interaction of histone H3 with a NuRD repressor, may include:
(a) bringing into contact one or more components of the NuRD repressor complex and a histone H3 polypeptide in the presence of a test compound; and,
(b) determining interaction between the histone H3 polypeptide and the said one or more components.

The one or more components of the NuRD repressor complex and the histone H3 polypeptide may be brought together in the presence of a SET1 polypeptide. A reduction in the activity of the SET1 polypeptide in methylating the lys 4 residue of the histone H3 polypeptide may be determined by an increase in interaction and/or binding between the NuRD complex and the histone H3 polypeptide in the presence relative to the absence of the test compound.

Components of the NuRD complex may include HDAC1, HDAC2, Mi-2β, Rbap48, Rbap46, MTA1, MTA2 and MBD3 (Zhang et al (1998) Cell 95(2)279–289). Histone H3 polypeptides are described above.

Interaction and/or binding may be determined by any convenient technique as described above. A agent identified and/or obtained using such a method may be useful in the modulation of transcriptional activation.

Other aspects of the present invention relate to the tri-methylation of histone H3 lysine 4 by a SET1 polypeptide and the effect of lys 4 tri-methylation on transcriptional activation.

A method of identifying transcriptionally active chromatin may comprise;
determining the presence or absence of a trimethylated Lys 4 residue in a histone H3 polypeptide of said chromatin.

The presence of a trimethylated Lys4 residue in a histone H3 polypeptide of said chromatin is indicative that said chromatin is transcriptionally active.

The presence or absence of a trimethylated Lys 4 may be determined by any convenient means. For example, said chromatin region may be contacted with an antibody which binds specifically to a histone H3 polypeptide which is trimethylated at Lys 4.

Various further aspects and embodiments of the present invention will be apparent to those skilled in the art in view of the present disclosure.

Certain aspects and embodiments of the invention will now be illustrated by way of example and with reference to the figure described below.

Figure 1:
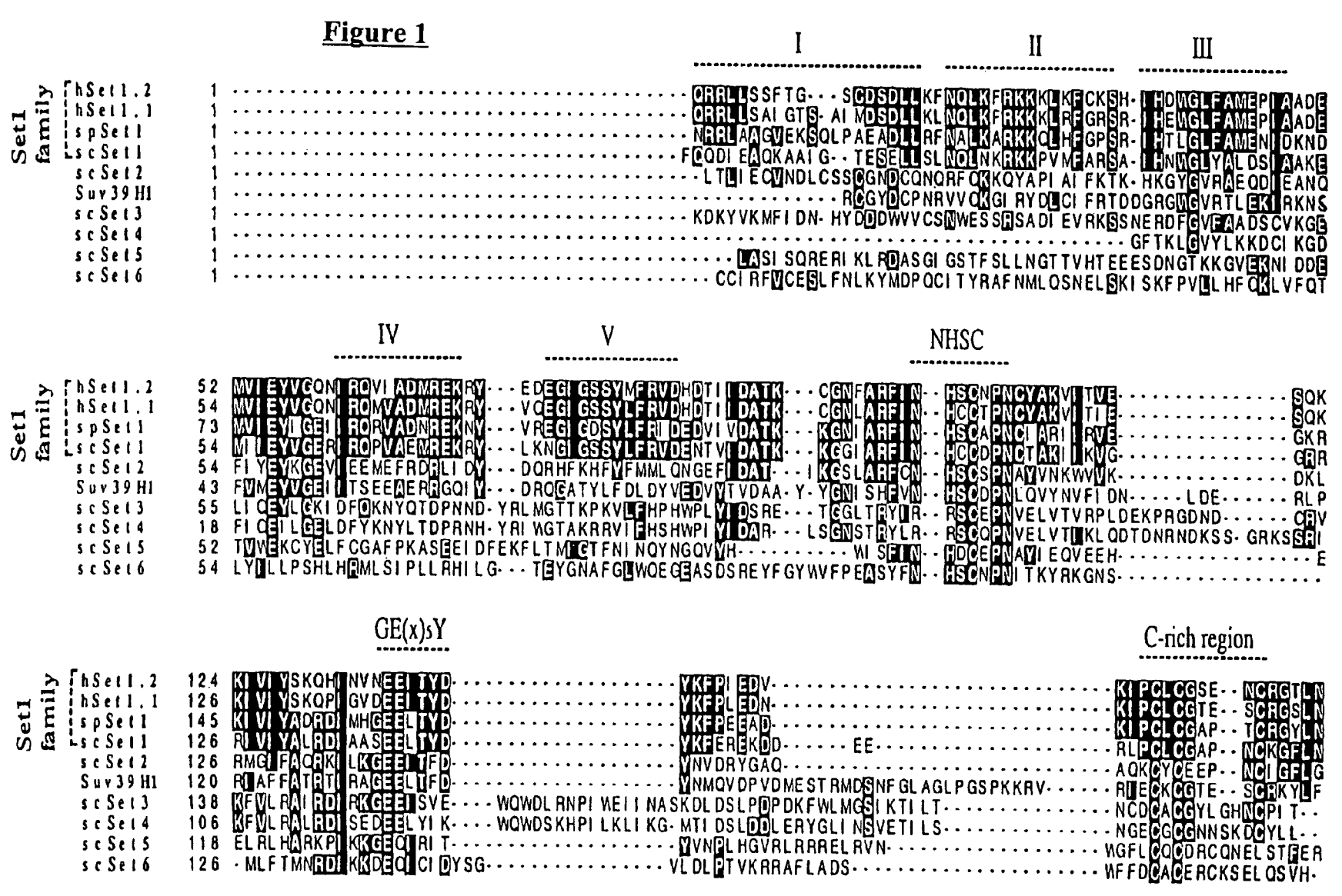

FIG. 1 shows sequence alignments within the SET domains and flanking sequences of yeast proteins containing SET domains, human homlogues of SET1 and the human histone H3 lysine 9 methylase Suv39h1. hSet1.1, human KiAA0339; hSet1.2, human KIAA1076; sp Set1, *S. pombe* SPCC306.04c; sc Set1, *S. cerevisiae* Set1p; sc Set2, *S. cerevisiae* Set2p; Suv39H1, human Suvar 39H1; sc Set3, *S. cerevisiae* YJL105W; sc Set4, *S. cerevisiae* YKRO29C; sc Set5, *S. cerevisiae* YHR207C; sc Set6, *S. cerevisiae* YPL165C. Alignments were calculated as follows: Clustal W1.8 (DNA-Protein)-Global progressive (BCM), BOXADE 3.21, Consensus line: No consensus, Fraction of sequences (that must agree for shading): 0.5.

FIG. 2 shows sequence alignments within the SET domains and flanking sequences of SET1 and SET2 polypeptides. hSet1.1, human KiAA0339; hSet1.2, human KIAA1076; sc Sett, *S. cerevisiae* Set1p; spSet2, *S. pombe* SPAC29B12; sc Set2, *S. cerevisiae* Set2p; hSet2.1, human KlAA1732; hSet2.2, human HSPCO69; hSet2.3, human AJ238403; WHSC17 human WHSC1.

FIG. 5 shows a schematic diagram of various methylated and unmethylated histone H3 peptides used to purify a specific set of binding proteins. The C-terminus of each of the peptides was followed by GGC.

Figure 3:
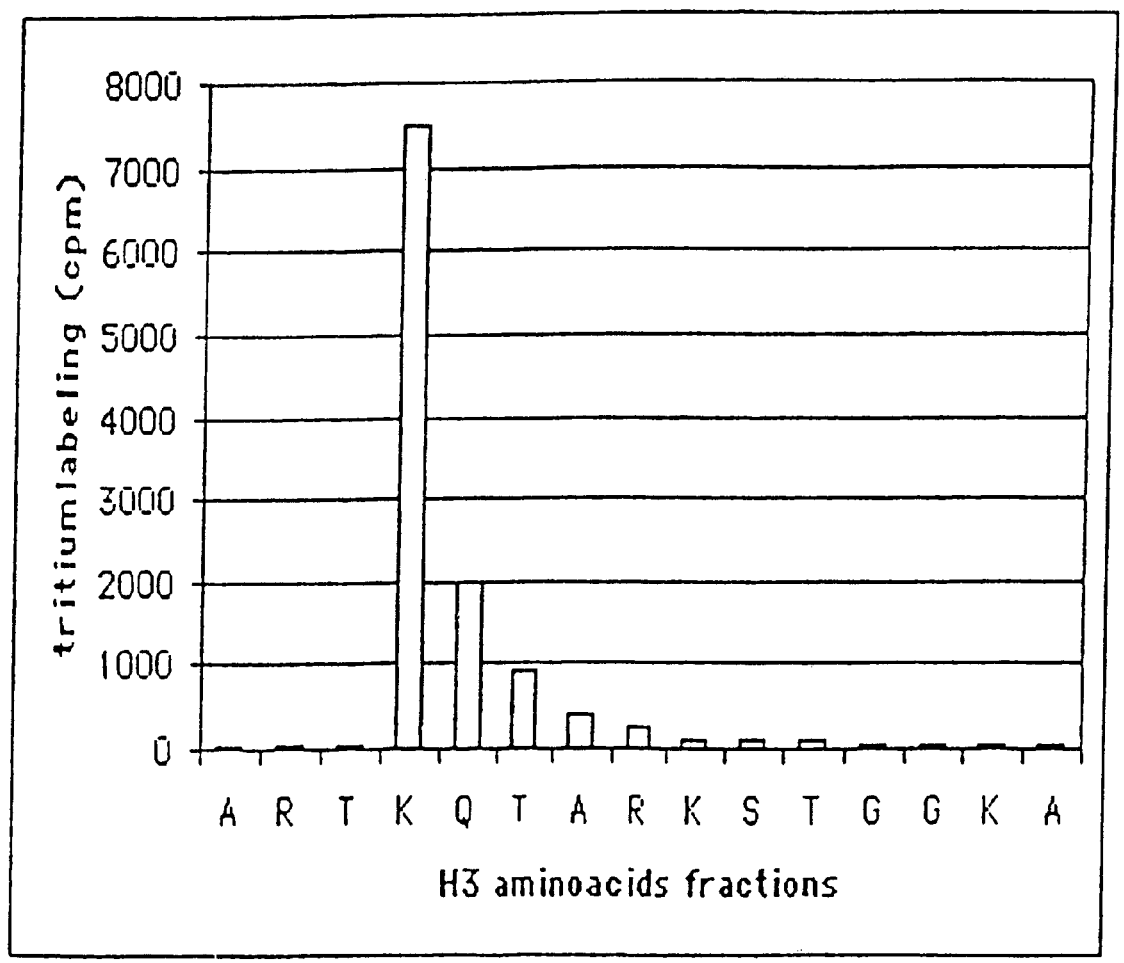
FIG. 3 shows the mapping of the methylation site of the *S. cerevisiae* SET1 in the histone H3 amino tail.
Figure 4:
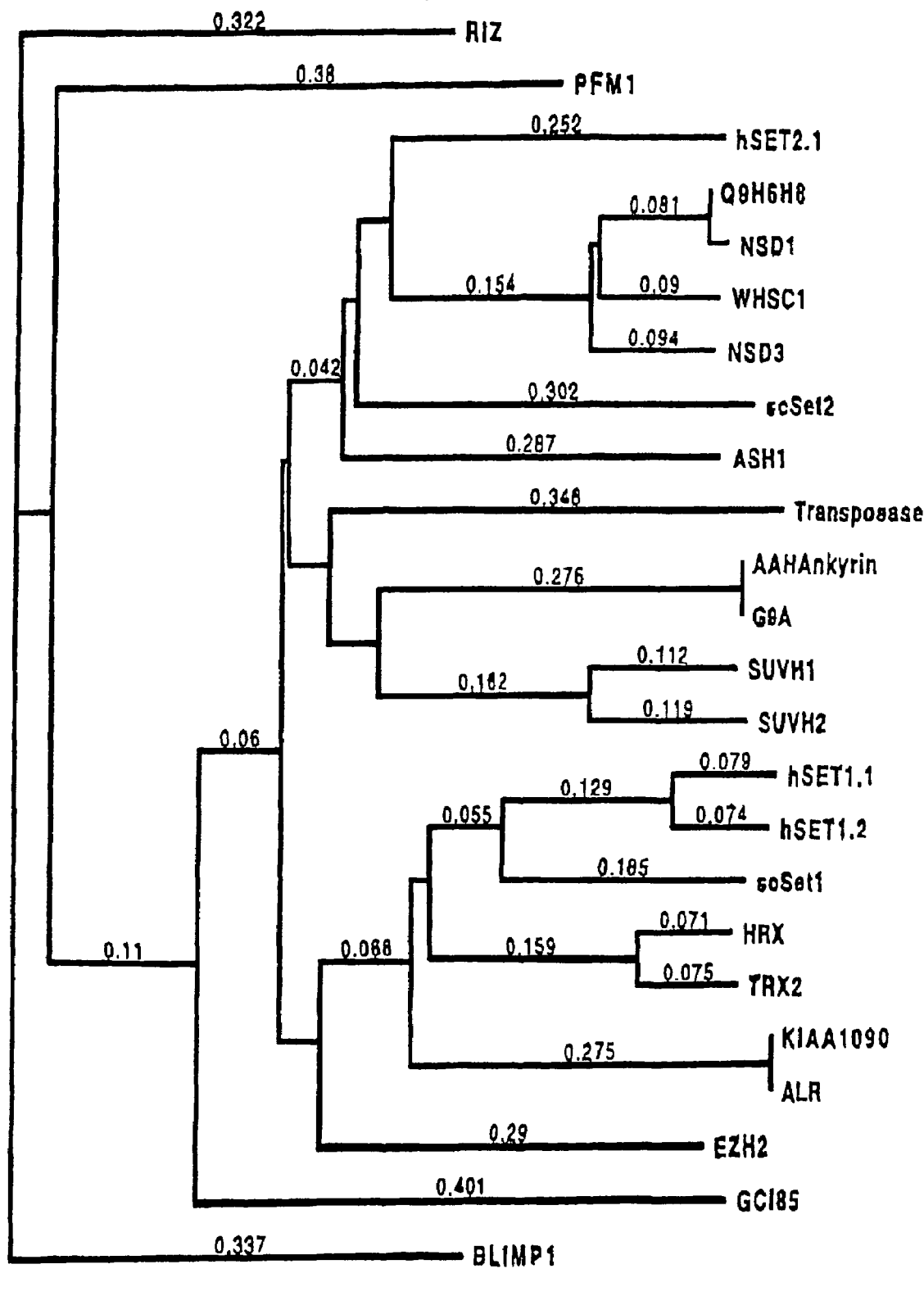
FIG. 4 shows a relationship tree between proteins which contain SET domains. The tree was compiled using the following multiple alignment parameters; program—ClustalW (v1.4), similarity matrix—blosum, Open Gap penalty—10.0, Extend Gap penalty—0.1, Delay Divergent—40%, Gap distance—8.

FIG. 7 shows a list of genes activated by SET1. To identify targets of SET1 mediated expression, transcription profiles of set1Δ yeast were determined. Potential targets were collated from genes down regulated in the mutant and assigned relative merit (P-value) using a gene-specific error model. Secondary effects were eliminated by disregarding genes also down regulated in general stress or in a sir2Δ profile (sir2Δ and sir1Δ yeast both exhibit downstream effects secondary to derepression of the silent mating loci).

Table 1 shows % identity within the SET Domain among the SET1 and SET2 Families. The table was compiled using the following parameters; program—MacVector 6.5, matrix—BLOSUM 30, Clustal alignment—pairwise alignment, Open Gap penalty—1.0, Extend Gap penalty—0.1.

Table 2 shows a summary of the K4 methylation state at the promoter of constitutive genes, inositol regulated genes and methionine regulated genes. "–" means no methylation detected. "Di" means di-methylation detected at the promoter and "tri" means tri-methylation at the promoter. The growth conditions for activation and repression of the genes are described below.

EXPERIMENTAL

Materials and Methods

Purification of Yeast SET Protein

Yeast Set1p and Set6p were tagged at the N-terminus with a Protein A epitope from *S. aureus*. These proteins were expressed in the wild type strain RS453 (mat a, ade2, ura3, leu2, his3, trp1) and in the C 13 ABYS-86 strain (Matα ura3 leu2-3 his3-112 pra1-1 prb1-1 prc1-1 cps1-3). The tagged proteins with the expected size (PtA-Set1p, 160 Kda; PtA-Set6p, 55 Kda) were detected in total extract by western blot with Anti Protein A antibody (PAP, rabbit, DAKO-Z0113) 1:3000 dilution. PtA-Set1p and PtA-Set6p were purified by affinity to an IgG Sepharose column as described (Siniossoglou, S. et al (1996) Cell 84, 265–275). For each set of assays, 5 g of spheroplasts were homogenised in 50 ml of lysis buffer. The soluble supernatant (S) was passed through a column containing 200 μl of IgG beads.

Avoiding the elution step, the beads were washed with 25 ml of equilibration buffer. Then, 60 μl of beads were transferred to 3 eppendorf tubes, placed on ice, for the enzymatic reaction. The remaining 20 μl beads were re-suspended in 50 μl Laemli buffer, vortex and boiled for 3 min. Samples of "soluble supernatant, S" (30 μl, equivalent to 0.06% of the total soluble supernatant) and "eluted protein, E" (25 μl, equivalent to 5% of the total purified protein) were analysed by western blot with Anti Protein A antibody (PAP, rabbit, DAKO- Z0113) 1:3000 dilution.

Equilibration Buffer: 20 mM Tris-HCl pH 8.5; 0.05 mM DTT.

Methyltransferase Assay

The enzymatic assays were performed on a mixture of soluble histones from calf thymus (H2A, H2B, H3 and H4), Sigma; recombinant *xenopus* H3 or H3 deleted for the first 26 amino acids (Δtail H3).

For each reaction, 60 μg of calf histones or 20 μg of recombinant H3 were used. The following mixtures were prepared:

1) 60 μl of PtA-Set p beads (either Set1p, Set2p or Set6p)+30 μl of methylation buffer+2 μl of $^{14}$C-SAM (NEC-363 adenosyl-L-methionine, S-(methyl-$^{14}$C).
2) 60 μl of PtA-Set p beads (either Set1p, Set2p or Set6p)+30 μl of methylation buffer+3 μl of soluble histones (60 μg)+2 μl of 14C-SAM (NEC-363 adenosyl-L-methionine, S-(methyl-$^{14}$C).
3) 60 μl of PtA-Set p beads (either Set1p, Set2p or Set6p)+30 μl of methylation buffer+4 μl of recombinant xH3 (20 μg)+2 μl of 14C-SAM (NEC-363 adenosyl-Lmethionine, S-(methyl-14C).
4) 60 μl of IgG sepharose beads (previously equilibrated in methylation buffer)+30 μl of methylation buffer+3 μl of soluble histones (60 μg)+2 μl of 14C-SAM (NEC-363 adenosyl-L-methionine, S-(methyl-14C).
5) 60 μl of IgG sepharose beads (previously equilibrated in methylation buffer)+30 μl of methylation buffer+4 μl of recombinant xH3 (20 μg)+2 μl of 14C-SAM (NEC-363 adenosyl-L-methionine, S-(methyl-14C).

Methylation Buffer: 50 mM Tris-HCl pH 8.5; 20 mM K Cl, 10 mM MgCl2, 10 mM -mercaptoethanol, 0.05 mM DTT, 250 mM sucrose, 0.2% dodecyl-β-D-maltoside.

When assayed, the recombinant *xenopus* H3 deleted for the 26 first amino acids (xgH3) was used at 10 μg/reaction.

The microfuge tubes were incubated at 30° C. during 2 hours with shaking. After that, 15 μl of 4× (protein sample buffer) were added to each reaction (the total liquid vol. of each reaction should be around 45 μl). The samples were boiled for 3 minutes. The histones were separated in a 1.5 mm, 20% acrylamide gel, run at 200 V during 1 hour and 15 minutes and transferred to nitro-cellulose membranes by standard procedures. The nitro-cellulose membrane was exposed to Kodak Biomax MS film with Biomax Transcreen-LE intensifying screen at −80 C during 36–48 h.

Mapping of Site of Methylation within Histone H3

Histone H3 was methylated by SET1 as described herein with a $^{14}$C-methyl group. The methylated residue was then identified using N terminal sequence analysis as described in Rein D. and Speicher D. Current Protocols in Protein Science (1997) 11.10.01–11.10.38.

Briefly, A stained protein band was excised from a PVDF membrane, sonicated in a both sonicator and sequenced using a Hewlett-Packard Model G 100SA sequencing system. Sequencing was carried out according to the manufacturer's instructions and PTH (phenylthiohydantoin) amino acids from each sequencer cycle were separated by in-line HPLC to provide sequence data.

Expression Profiling

The set1Δ mutant and its parent strain UCC1001 were grown in parallel in YPD media at 30° C. to an OD$_{600}$ of 1.0. Poly (A) RNA was isolated and reverse transcribed incorporating amino-allyl dUTP. The resulting DNA probe was labeled with reactive Cy5 (mutant) or Cy3 (parent strain) dye and hybridized to a spotted cDNA microarray containing the yeast open reading frames as described in Carroll et al (2001) PNAS 98 12578–12583 and DeRisi et al (1997) Science 278 680–686. Microarrays were analyzed using a GenePix4000A scanner and GENEPIX 3.0 software. Candidate SET1 regulated genes were identified from duplicate experiments using a gene specific error model described previously (Hughes et al Cell (2000) 102 109–126).

Northern Blots and ChIPs

Northern blots and ChiPs were done as described in Kent et al Genes Dev (2001) 15 619–626, except that for ChIP 5μl of Tri-meK4 H3 antibody and 2 μl of Di-me K4 H3 antibody were used and protein A-sepharose beads were pre-incubated with 1.5 μg of sonicated salmon sperm DNA for 30 minutes. For the ChIPs experiments, the cell were grown o/n in minimal medium lacking inositol (medium −ino), then diluted to OD600: 0.15 in minimal medium −inositol or the same one supplemented with 100 mg/L inositol (medium +ino) and grown to OD600: 1.2 and then processed for chromatin preparation.

Samples from medium −methionine and +methionine were prepared in the same way except that the medium was supplemented.

Affinity Purification from Hela Nuclear Extract

Histone peptides which were trimethylated at different lysine residues, were made using standard techniques. The C-terminus of the peptides contained a 2 glycine spacer followed by a cysteine. The peptides were immobilised onto Sulfolink Coupling gel (Pierce) via the C-terminal cysteine, at a concentration of 1 mg/ml.

Hela nuclear extract (Computer Cell Culture Centre, Belgium) was diluted in IPH buffer (50 mM Tris pH8, 150 mM NaCI, 5 mM EDT A. 0.5% NP-40 v/v) to a final protein concentration of 4 mg/ml and pre-cleared.

Affinity purifications were done with 5 µl of sepharose-linked peptide and 150 µl of diluted Hela nuclear extract. Competitor peptide was added to a final concentration of 150 µg/ml, where used. The purifications were incubated for 90 minutes on a wheel at 4° C. and washed 3 times in IPH before resolution on an 8% SDS-PAGE gel. For column purification of complex, 2 ml of diluted Hela nuclear extract was poured twice over a micro-column of 100 µl of sepharose-linked unmethylated H3 peptide. The column was washed with 4 column volumes of IPH and bound proteins were eluted in 250 mM NaCl IPH. Eluted fractions containing the complex were made up to 150 µl in IPH and rebound to 5 µl of H3 peptide sepharose, as above. Bound proteins were visualised by silver staining as described previously (Morrissey (1981) 117(2) 307–310).

Mass Spectrometry Identification of Proteins

Proteins that rebound un-methylated peptide after column purification were excised from an 8% coomassie stained gel with a protein-free razor blade. Proteins were digested in-gel with trypsin. After overnight incubation at 30° C., a 0.5 µl aliquot from the digest was spotted on the MALDI target for fingerprinting. The remaining digest was purified using C18 Zip-Tips prior ESI-MS. Peptide Mass Fingerprints were taken with a MALDI instrument from Micromas fitted with Delayed Extraction, using Alpha-cyano-cinnamic acid dissolved in 50% Acetonitrile: 0.1% TFA as matrix. CID fragmentation spectra from peptides were taken with an Ion-trap instrument (LCQ-Decca) from ThermoQuest. Protein databases were searched with the mass spectrometry data using the programs Mascot, http://matrixscience.com (Mass fingerprinting and fragmentation spectra) and Profound, http://129.85.19.192 (mass fingerprinting data).

Deacetylase Assays

Histone peptide affinity purifications from Hela nuclear extract were re-suspended in 100 µl of fresh IPH buffer containing 150,000 cpm of [$^3$H]-labelled acetylated H4 peptide. Reactions were incubated at 37° C. for 120 minutes, with regular mixing. Reactions were stopped by the addition of 65 µl of acid mix (1 M HCl, 0.16 M acetic acid). 700 µl of ethylacetate was added and tubes were vortexed vigorously for 20 seconds. Phases were separated by centrifugation at 13500 rpm for 1 min. 500 µl of the upper phase (ethylacetate) was removed and mixed with 1 ml of scintillant (Optiphase™, Wallac). Release of ($^3$H)-acetate from the H4 peptide was measured in counts per minute (cpm) using a scintillation counter (Beckmann LS6000SC).

Western Blots, Antibodies and Immunoprecipitations

Bound proteins were resolved on 8% SDS-PAGE gel, blotted to nitrocellulose and blocked overnight (4% non-fat milk/0.5% Tween 20 v/v). Blots were probed with the following antibodies for 1 hour at room temperature: anti-Rbap48 (Genetex, 11g10, 1 µg/ml), anti-DNMT1 (NEB-231, 1 in 1000), anti-Sin3 (Santa Cruz 994, 1 µg/ml) and anti-p60 (1 in 1000). Blots were washed in blocking buffer, incubated with HRP linked secondary antibodies (Abcam) and visualised with ECL (Amersham). NuRD immunoprecipitations were done by incubating 500 µl of diluted Hela nuclear extract with anti-MTA2 antibody (Santa Cruz 9447: 1 µg/ml) and 15 µl of protein A/G bead mix (Amersham) for 5–12 hours at 4° C.

Precipitations were washed 3 times with IPH before resolution on a 20% SDS-PAGE gel. After blotting to nitrocellulose and blocking (5% BSA/0.5% Tween 20) for 1 hour at room temperature, the blots were probed overnight with anti-MBD3 (Santa Cruz 9402, 1 µg/ml), anti-H3 (500 ng/ml) or anti-H4 (Abcam ab7311, 500 ng/ml).

Blots were washed briefly with BSA blocking buffer, incubated with HRP linked secondary antibody and visualised as above.

Results

S. cerevisiae SET1 and SET2 are Histone

Methyltransferases (HMTs)

PtA tagged SET1p, SET2p and SET6p were purified from S. cerevisiae by IgG sepharose chromatography. Western blotting revealed a strong band in each of the eluted protein fractions corresponding to full-length PtA-SET1p, PtA-SET2p and PtA-SET3p, respectively.

Approximately 10 µg of purified PtA-SET1p, PtA-SET2p or PtA-SET6p were assayed for methyltransferase activity on 60 µg of a mixture of calf thymus soluble histones (H2A, H2B, H3 and H4) or 20 µg of recombinant xenopus histone H3 in the presence of ($^{14}$C-Me) S-adenosyl methionine. Autoradiograms were developed after 48 hours exposure.

No methylation was observed for PtA-SET1p, PtA-SET2p or PtA-SET6p in the absence of calf or recombinant histones.

PtA-SET1p and PtA-SET2p were observed to methylate recombinant Xenopus histone H3. When the preparation of histones H2A, H2B; H3 and H4 was used, PtA-SET1p and PtA-SET2p were observed to specifically methylate histone H3.

No methylation activity was observed for PtA-SET6p in the presence of histones H2A, H2B, H3 and H4 or the presence of recombinant Xenopus histone H3.

The Methyltransferase Activity of SET1 is Specific for Lysine 4.

A truncated recombinant Xenopus H3 histone containing lacking the first 26 N terminal residues was compared with the full length Xenopus H3 histone as a substrate for PtA-SET1p and PtA-SET2p.

For each assay, 20 µg of recombinant Xenopus H3 histone and 10 µg of PtA-SET1p were incubated in the presence of ($^{14}$C-Me) S-adenosyl methionine. Autoradiograms showing the presence of $^{14}$C label were developed after 48 hours. The presence of substrates on the gel was confirmed by Ponceau staining.

No methylation was observed in the absence of a histone H3 substrate.

Both PtA-SET1p and PtA-SET2p were observed to methylate full length Xenopus histone H3.

No methylation by PtA-SET1p of the Xenopus histone H3 with the N terminal deletion was observed but PtA-SET2p was observed to methylate this truncated protein.

These results demonstrate that PtA-SET1p methylates histone H3 within the N terminal 26 amino acid residues of histone H3 whereas PtA-SET2p methylates outside this amino tail region, within the core of the histone H3 polypeptide.

Mapping of the Methylation Site within the H3 Amino Tail

Xenopus H3 histone labelled with a $^{14}$C-methyl group by PtA-SET1p as described above, was sequenced by sequential Edman degradation and fractions corresponding to each amino acid cycle were collected and counted by scintillation counting. The results are shown in FIG. 3. The N terminal sequence of Xenopus histone H3 is shown underneath corresponding fraction.

These results show that the lysine 4 residue of histone H3 is specifically methylated by PtA-SET1p. No methylation of lysine 9 is observed.

SET polypeptides as described herein are shown to specifically methylate histone H3 at residues other than lysine 9.

SET1 polypeptides methylate the lysine 4 residue while SET2 polypeptides methylate the core of histone H3, outside the amino tail.

The Histone H3 N-terminus Binds a Set of Proteins When Unmethylated at Lysine 4

Differently methylated histone peptides were used in pull downs assays from Hela nuclear extract and the bound proteins analysed by silver stain.

The histone peptides used were trimethylated at lysine 4 (K4), lysine 9 (K9) or both (K4+K9) and two control peptides of unmethylated H3 and H4 tails (FIG. 5). These peptides were immobilised onto sepharose beads via a C-terminal cysteine residue and used to affinity purify proteins from Hela nuclear extract.

Although some proteins were found to specifically bind to the methylated peptides, a number of proteins were also observed to be specifically purified by the unmethylated H3 peptide.

This set of proteins was also observed to be purified by the K9 methylated H3 peptide, but not by a peptide methylated at K4, or K4 and K9, or by an unmethylated H4 peptide. This indicates that these proteins only bind to histone H3 N-termini when lysine 4 is unmethylated and that methylation of lysine 9 does not disrupt the binding of the complex.

To confirm the specificity of the proteins binding to unmethylated H3 peptide, pull downs were done in the presence or absence of competitor peptide. The set of proteins bound to the unmethylated peptide was observed to be competed away by peptides unmethylated at K4, but not by peptides with a methylated K4.

The Set of Proteins Bound to Unmethylated H3 Tails is the NuRD Complex

The set of proteins, putatively components of a binding complex, identified above were purified from Hela nuclear extract over a column of unmethylated H3 peptide. The column-purified proteins, once eluted in high salt, were rebound to unmethylated peptide in a pull down assay. The rebound proteins were resolved by SDS-PAGE and silver stained. This purified source of the putative complex was used for mass spectrometry identification of the components.

The sub-units of the complex identified in this way include the histone deacetylases HDAC1/2, the ATPase chromatin-remodelling enzyme Mi-2β, the RB associated proteins Rbap48/46, the metastasis-associated antigens MTA1/2 and the methyl CpG binding domain MBD3. These are all known components of the NuRD complex (Zhang et al (1998) Cell 95(2) 279–289, Zhang et al (1999) Genes Dev 13(15) 1924–1935, Xue et al (1998) Mol Cell 2(6) 851–861).

Several components of the NuRD complex have been identified in other deacetylase complexes (Knoepfler, P. S. et al (1999) Cell 99, 447–450). The purified complex with antibodies against other deacetylase complex components. Rbap48 protein was detected, whereas DNMT1 and Sin3 (present in distinct deacetylase complexes: Robertson, K. D. et al (2000) Nat Genet 25(3), 338–42. 22, Zhang, Y et al (1997) Cell 89(3), 357–64), were absent from the H3 purified complex. Rbap48 is also present in the CAF-1 (chromatin assembly factor 1) complex (Ridgway, P. et al (2000) J Cell Sci 113{pt 15), 2647–58.). However a western blot with the p60 subunit of CAF-1 did not detect CAF-1 in the H3 purified complex.

Figure 6:
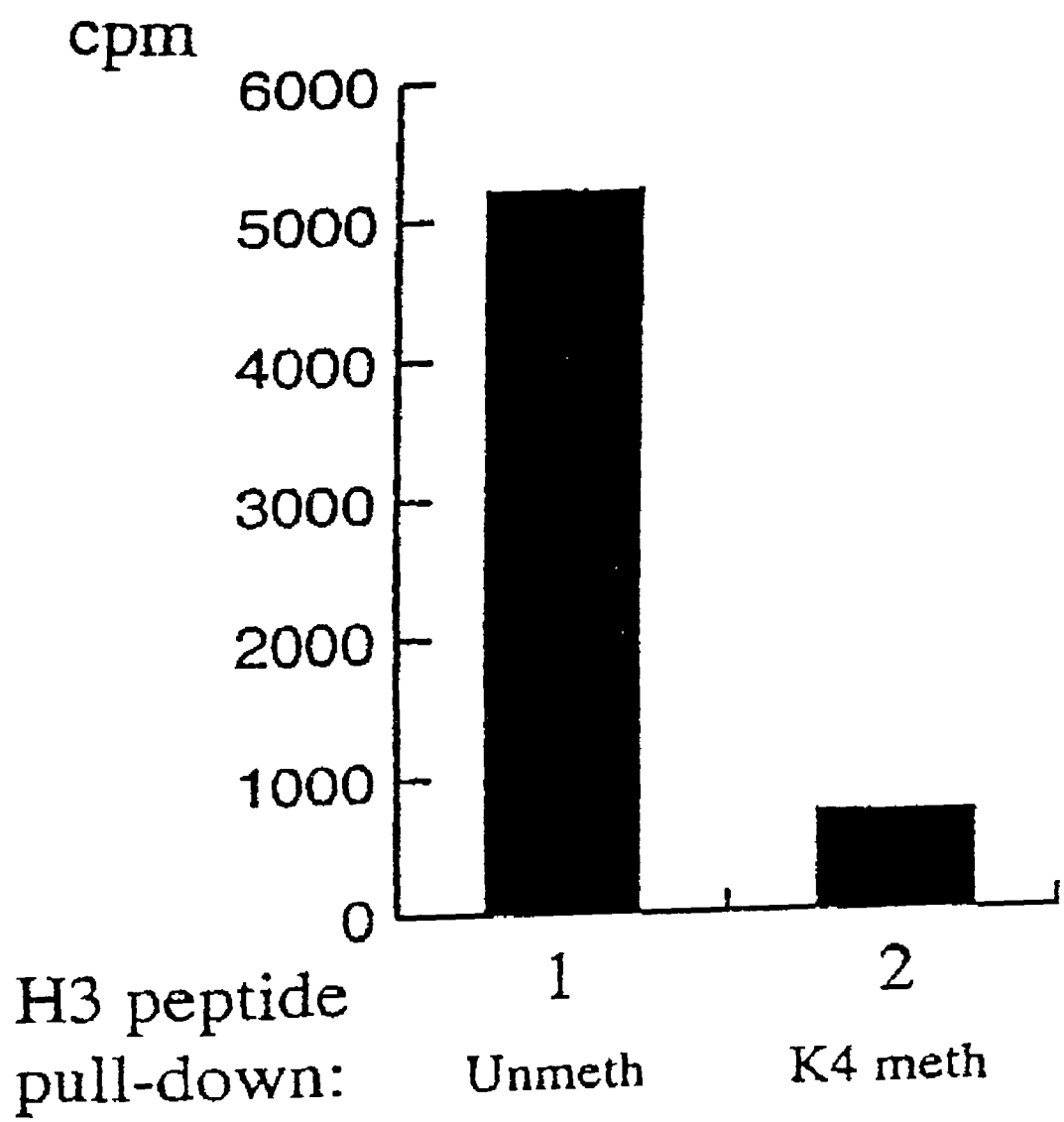
FIG. 6 shows the deacetylase activity and released tritiated acetate, as measured by scintillation counting (c pm=counts per minute) from proteins bound to the unmethylated and methylated histone H3 peptide in pull down assays.

To establish if NuRD has deacetylase activity when affinity purified on unmethylated H3 peptide, peptide pull downs were assayed for deacetylase activity. Unmethylated H3 peptide was found to associate with a significant level of histone deacetylase (HDAC) activity (FIG. 6). In contrast, a peptide methylated at K4 pulled down background levels of HDAC activity. This indicates that the deacetylase activity of the NuRD complex is not compromised when it is associated with the unmethylated histone H3 tail.

NuRD Complex Associates with Native Histone H3 Only When Unmethylated at Lysine 4

Previous studies have shown that the NuRD complex can be immunoprecipitated using anti-MTA2 antibodies (Zhang et al (1999) supra). MT A2 antibodies were observed to precipitate MBD3 (a component of NuRD) as well as histone H3 and H4, as detected by western blot with the respective antibodies.

The immunoprecipitated histones were found to be efficiently competed away by the unmethylated peptide, but not by the K4 methylated peptide. These data indicate that the NuRD complex associates with unmethylated native histone H3 (and interacts indirectly with H4 via H3).

Methylation Status of K4 of Histone H3

The ε amino group of lysine residues may be mono-, di- or tri-methylated (me). Antibodies were raised to specifically recognize either the di-me or tri-me state of K4 H3. An antibody raised against di-me K4 was found to recognize H3 from a purified source of histones and is effectively competed by a di-me but not a tri-me K4 H3 peptide. An antibody raised against tri-me K4 was found to be specifically competed by the tri-me but not di-me K4 H3 peptide. Both antibodies were found to selectively recognise histone H3 in a total yeast extract. Neither antibody recognised H3 from a yeast strain containing a K4 H3 mutation to alanine (K4A) and neither antibody recognised bacterially produced recombinant, unmethylated H3.

Both Di- and Tri-me K4 antibodies were found to recognise histone H3 after it has been methylated by SET1. Deletion of SET1 abolishes recognition of histone H3 by the Di- and Tri-me K4 antibodies, whereas deletion of other S. cerevisiae SET genes (SET2, 3, 4, 5 and 6) has no effect.

To establish if the bi- or Tri-me state is linked to gene activity, we investigated whether SETI can act as an activator of transcription and identified genes positively regulated by SET1.

Transcriptional profiling of yeast deficient in SET1 waS therefore carried out and 200 genes were identified whose activity is reduced in the absence of SET1. FIG. 7 shows a list of the top twenty genes whose transcription is reduced between 1.6 and 2.1 fold in set1Δ strain relative to WT yeast. Northern blot analysis of one of these genes PPH3, confirms that the mRNA expression of this gene is indeed reduced in the set1Δ strain. This indicates that SET1 positively regulates transcription.

We next established whether the SET1 activated genes were methylated at K4H3 and identified the methylation state of K4. The PPH3 gene, as well as two of the other SET1-dependent genes, HAM1 and NUP 170, were investigated. The use of Di-me and Tri-me specific antibodies in chromatin immunoprecipitation (ChiPs) showed that all three genes have Di- and Tri-me K4 H3 associated with their promoter.

Since the expression profiling was done from yeast grown in rich medium, all three of these genes, and indeed all the SET1-regulated genes in FIG. 7, are constitutively active.

The K4 H3 methylation status of a set of genes whose activity can be regulated was then investigated using genes that can be activated by either inositol or methionine deprivation. When the INO1 gene is repressed, K4 H3 was found to be Di-me but not Tri-me. However, when the gene is active, K4 H3 Di-me was still observed but Tri-me also became apparent. Two other inositol regulated genes INO2 and INO4 also showed the presence of Tri-me K4 H3 only when active.

Analysis of an independent metabolic pathway, where genes are actively transcribed in the absence of methionine, showed that the MET16 gene has Tri-me K4 H3 only when the gene is active and Di-me only when repressed. Another methionine regulated gene, MET17, showed no Di-me K4H3, either when active or repressed but tri-me K4 H3 appeared when the gene became active. The K4 methylation patterns we observed at all the genes analysed here were not restricted to promoter regions but were also observed when probes in the coding region were used.

These results (summarized in Table 2) indicate that the trimethyl state of K4H3 is unambiguously linked to active transcription. When genes are repressed, tri-me K4 H3 is not observed. In contrast, Di-me K4 H3 is often present in repressed genes but is also present on some active genes. This is consistent with previously reported findings at the chicken beta-globin locus, where Di-me K4 H3 is detected on large euchromatic regions encompassing both active and inactive genes (Litt et al *Science* 293 2453–5 (2001)). Di-me K4 H3 may determine a transcriptionally active state "poised" for stimulation.

These findings demonstrate that SET1 is an activator of transcription and uncover a new level of regulation of K4 H3 function, by virtue of methylation status.

Methylation of histone H3 by SET polypeptides plays an important role in the regulation of transcriptional activity and the control of cellular proliferation. Manipulation of the SET polypeptide histone methyltransferase activity may therefore be used in the treatment of conditions associated with cellular proliferation, such as cancer.

TABLE 1

|        | scSET1 | pSET1 | hSET1.1 | hSET1.2 | scSET2 | spSET2 | hSET2 | WHSC1 | Suv39H |
|--------|--------|-------|---------|---------|--------|--------|-------|-------|--------|
| scSET1 | 100%   | 51%   | 57%     | 54%     | 29%    | 30%    | 28%   | 33%   | 28%    |
| spSET1 |        | 100%  | 55%     | 54%     | 29%    | 32%    | 30%   | 30%   | 28%    |
| hSET1.1|        |       | 100%    | 82%     | 25.5%  | 28%    | 28%   | 27.5% | 25%    |
| hSET1.2|        |       |         | 100%    | 27%    | 30%    | 30%   | 31%   | 24%    |
| scSET2 |        |       |         |         | 100%   | 61%    | 47%   | 41.5% | 31%    |
| spSET2 |        |       |         |         |        | 100%   | 49%   | 40%   | 29%    |
| hSET2  |        |       |         |         |        |        | 100%  | 49%   | 31%    |
| WHSC1  |        |       |         |         |        |        |       | 100%  | 30%    |
| Suv39H |        |       |         |         |        |        |       |       | 100%   |

TABLE 2

| | Gene | Repressed | | Active | |
|---|---|---|---|---|---|
| Constitutively active genes | PPH3 | | | Di | Tri |
| | HAM1 | | | Di | Tri |
| | NUP170 | | | Di | Tri |
| Inositol regulated genes | INO1 | Di | | Di | Tri |
| | INO2 | Di | | Di | Tri |
| | INO4 | Di | | Di | Tri |
| Methionine regulated genes | MET16 | Di | | — | Tri |
| | MET17 | — | | — | Tri |

The invention claimed is:

1. A method of identifying transcriptionally active chromatin comprising:
    contacting chromatin with an antibody that binds specifically to a histone H3 polypeptide which is trimethylated at Lys4, and
    determining the presence or absence of binding of said antibody to said chromatin,
    the presence of binding of said antibody to said chromatin being indicative that said chromatin is transcriptionally active chromatin.

* * * * *